(12) United States Patent
Spenciner

(10) Patent No.: US 12,357,447 B2
(45) Date of Patent: Jul. 15, 2025

(54) SYSTEMS AND METHODS FOR PREPARING REINFORCED GRAFT CONSTRUCTS

(71) Applicant: Medos International Sarl, Le Locle (CH)

(72) Inventor: David B. Spenciner, North Attleboro, MA (US)

(73) Assignee: Medos International Sàrl, Le Locle (CH)

( * ) Notice: Subject to any disclaimer, the term of this patent is extended or adjusted under 35 U.S.C. 154(b) by 324 days.

(21) Appl. No.: 17/979,383

(22) Filed: Nov. 2, 2022

(65) Prior Publication Data

US 2023/0092231 A1 Mar. 23, 2023

Related U.S. Application Data

(60) Continuation of application No. 17/011,628, filed on Sep. 3, 2020, now Pat. No. 11,517,420, which is a continuation of application No. 15/462,121, filed on Mar. 17, 2017, now Pat. No. 10,779,932, which is a division of application No. 14/584,235, filed on Dec. 29, 2014, now Pat. No. 9,622,742.

(51) Int. Cl.
*A61F 2/08* (2006.01)
*A61B 17/04* (2006.01)
*A61B 17/06* (2006.01)

(52) U.S. Cl.
CPC ............ *A61F 2/08* (2013.01); *A61B 17/0482* (2013.01); *A61B 17/06066* (2013.01); *A61B 17/06166* (2013.01); *A61F 2220/0075* (2013.01)

(58) Field of Classification Search
CPC . A61F 2/08; A61F 2220/0075; A61B 17/0482
See application file for complete search history.

(56) References Cited

U.S. PATENT DOCUMENTS

| | | | |
|---|---|---|---|
| 5,306,301 A | 4/1994 | Graf et al. | |
| 5,645,588 A | 7/1997 | Graf et al. | |
| 6,235,057 B1 * | 5/2001 | Roger | A61F 2/0811 623/13.12 |
| 8,202,318 B2 | 6/2012 | Willobee | |
| 8,291,544 B2 | 10/2012 | Chen et al. | |
| 8,298,247 B2 | 10/2012 | Sterrett et al. | |
| 8,298,284 B2 | 10/2012 | Cassani | |
| 8,460,350 B2 | 6/2013 | Albertorio et al. | |

(Continued)

*Primary Examiner* — Christopher D. Prone
(74) *Attorney, Agent, or Firm* — Barnes & Thornburg LLP

(57) ABSTRACT

Systems and methods for preparing a tissue repair construct for a ligament reconstruction procedure using a reinforced whip-stitching are provided. The described techniques include passing a needle having suture tails attached thereto through a first surface of a graft at an origin point so that a portion of the suture tails exits on a second, opposite surface of the graft while a terminal length of the suture tails is maintained on the first surface of the graft. Multiple suture loops are formed by repeatedly passing the needle with the suture tails around opposite sides of the graft and through the first surface of the graft at subsequent entry points spaced apart along a length of the graft. Each loop is formed so that the construct is reinforced by having a terminal length of each of the suture tails disposed between the first surface of the graft and the loop.

20 Claims, 7 Drawing Sheets

(56) References Cited

U.S. PATENT DOCUMENTS

| | | |
|---|---|---|
| 8,591,544 B2 | 11/2013 | Jolly et al. |
| 8,591,578 B2 | 11/2013 | Albertorio et al. |
| 8,663,324 B2 | 3/2014 | Schmieding et al. |
| 9,622,742 B2 | 4/2017 | Spenciner |
| 10,779,932 B2 | 9/2020 | Spenciner |
| 11,517,420 B2 | 12/2022 | Spenciner |
| 2007/0250163 A1 | 10/2007 | Cassani |
| 2009/0018655 A1 | 1/2009 | Brunelle et al. |
| 2009/0105754 A1 | 4/2009 | Sethi |
| 2010/0249802 A1 | 9/2010 | May et al. |
| 2012/0046746 A1 | 2/2012 | Konicek |
| 2012/0253465 A1* | 10/2012 | Missos .................... A61F 2/08 623/13.19 |
| 2013/0023907 A1 | 1/2013 | Sterrett et al. |
| 2013/0023927 A1 | 1/2013 | Cassani |
| 2014/0074239 A1 | 3/2014 | Albertorio et al. |
| 2014/0277448 A1 | 9/2014 | Guerra et al. |
| 2016/0175088 A1 | 6/2016 | Sengun |
| 2016/0183936 A1 | 6/2016 | Spenciner |
| 2017/0189162 A1 | 7/2017 | Spenciner |
| 2021/0007840 A1 | 1/2021 | Spenciner |

* cited by examiner

SYSTEMS AND METHODS FOR PREPARING REINFORCED GRAFT CONSTRUCTS

CROSS REFERENCE TO RELATED APPLICATIONS

This application is a continuation of U.S. patent application Ser. No. 17/011,628 (now U.S. Pat. No. 11,517,420), filed on Sep. 3, 2020, and entitled "Systems and Methods for Preparing Reinforced Graft Constructs," which is a continuation of U.S. patent application Ser. No. 15/462,121 (now U.S. Pat. No. 10,779,932), filed on Mar. 17, 2017, and entitled "Systems and Methods for Preparing Reinforced Graft Constructs," which is a divisional of U.S. patent application Ser. No. 14/584,235 (now U.S. Pat. No. 9,622,742), filed on Dec. 29, 2014, and entitled "Systems and Methods for Preparing Reinforced Graft Constructs," which are hereby incorporated by reference in their entirety.

FIELD

Systems and methods are provided for preparing graft constructs with reinforced whip-stitching.

BACKGROUND

A ligament is a piece of fibrous tissue which connects one bone to another within the body. Ligaments are frequently damaged (e.g., detached, torn or ruptured) as the result of injury or accident. A damaged ligament can impede proper stability and motion of a joint and cause significant pain. When ligaments are damaged, surgical reconstruction can be necessary, as the ligaments may not regenerate on their own. A damaged ligament can be replaced or repaired using various procedures, a choice of which can depend on a particular ligament to be restored and on the extent of the damage.

An example of a ligament that is frequently damaged as a result of injury, overexertion, aging and/or accident is the anterior cruciate ligament (ACL) that extends between a top of the tibia and a bottom of the femur. Another ligament that is often damaged and may need to be replaced is a posterior cruciate ligament (PCL). A damaged ACL or PCL can cause instability of the knee joint, arthritis, and substantial pain.

ACL repair typically includes the use of a ligament graft replacement procedure which usually involves drilling bone tunnels through the tibia and the femur. Then a ligament graft, which may be an artificial ligament or harvested graft, such as a tendon, is passed through a tibial portion of the tunnel (sometimes referred to as "the tibial tunnel") across the interior of the joint, and up into a femoral portion of a tunnel (sometimes referred to as "the femoral tunnel"). One end of the ligament graft can then be secured in the femoral tunnel and another end of the graft is secured in the tibial tunnel, at the sites where the natural ligament attaches.

A common ligament reconstruction procedure involves using an autograft, which is a portion of the patient's own tendon that would replace the damaged natural ligament. The autograft is often a hamstring tendon, though other tendons can be used (e.g., a patellar tendon). The ligament graft can also be obtained from a donor ("allograft").

Ligament augmentation and replacement procedures typically require preparation of a harvested ligament graft using various techniques to secure the graft for passing through the drilled tunnels and to strengthen the graft prior to fixation. The preparation may involve cleaning and measuring the graft, and then affixing sutures to free ends thereof. The thus prepared graft can be tensioned prior to being inserted into the femoral and tibial tunnels.

Sutures are affixed to one or both free ends of the graft to reinforce it. The reinforcement is intended to maintain the structural integrity of the graft and to allow the graft to be properly tensioned when it is inserted into a tunnel for an ACL or PCL graft reconstruction. Sutures are affixed to the graft so that free suture ends that extend from one or both ends of the graft (which can be folded in half for the procedure) are used to secure the graft either directly or indirectly.

Although various graft preparation techniques exist for use in orthopedic surgery, such as, for example, ACL reconstruction, many of the developed approaches have certain drawbacks. In some instances, graft preparation can be time consuming and tedious. Simpler and quicker techniques often do not provide sufficient strength of attachment of the suture of the graft and may thus cause excessive elongation of the graft when a load is applied thereto. In other instances, a graft preparation technique can negatively affect the structural integrity of the graft.

Accordingly, there is a need for improved graft constructs and techniques for preparing such graft constructs while maintaining the desired structural integrity of the graft.

SUMMARY

In one aspect, a method of graft preparation is provided that in some embodiments includes passing a needle and a suture attached thereto and having first and second suture tails through a first surface of a graft at a first entry point remote from a first end of the graft so that the needle and a portion of the attached suture are passed to a second, opposite surface of the graft while maintaining a terminal length of each of the first and second suture tails on the first surface of the graft such that the terminal length of the suture tails extends in a first direction from the first entry point towards the first end of the graft. The method further includes passing the needle and the attached suture through the first surface at a second entry point longitudinally spaced apart from the first entry point in the first direction to the second surface with the suture tails disposed on opposite sides of the graft so that the suture forms a loop defined by the suture tails extending from the second entry point, to an exit point on the second surface of the graft and around opposite sides of the graft, the loop surrounding the terminal length of the first and second suture tails such that the terminal length of the suture tails is disposed between the first surface of the graft and the loop. The method also includes repeatedly passing the needle and the attached suture through the first surface at subsequent entry points longitudinally spaced apart from the first and second entry points in the first direction to the second surface to form multiple loops, each of the multiple loops spaced apart from adjacent loops in the first direction and each loop surrounding the terminal length of the first and second suture tails such that the terminal length of the suture tails is disposed between the first surface of the graft and the loop, and continuing the act of repeatedly passing until a final entry point in proximity to the first end of the graft is reached.

The method can vary in a number of ways. For example, the needle can be substantially a mid-point of the suture and the first and second suture tails attached to the needle can have approximately the same length. In some embodiments, the suture can be attached to the needle via an intermediate feature. A length of the suture tails can be approximately equal to a length of a portion of the graft between the first entry point and the first end of the graft. The suture can be a continuous, uninterrupted suture.

In some embodiments, the suture tails extend beyond the first end of the graft. Passing the needle and the attached suture through the first surface at the second and subsequent entry points can include passing the needle and the attached suture between the first and second suture tails. In some embodiments, passing the needle and the attached suture through the first surface at the second entry point can include passing the needle and the attached suture through the terminal length of at least one of the suture tails.

The method can further include passing a second needle and a second suture attached thereto and having third and fourth suture tails through the first surface of the graft at a third entry point remote from the second end of the graft so that the second needle and a portion of the attached second suture are passed to the second surface of the graft while maintaining a second terminal length of each of the third and fourth suture tails on the first surface of the graft such that the terminal length of the third and fourth suture tails extends in a second direction from the third entry point towards the second end of the graft. The method can further include passing the second needle and the second attached suture through the first surface at a fourth entry point longitudinally spaced apart from the third entry point in the second direction to the second surface with the third and fourth suture tails disposed on opposite sides of the graft so that the second suture forms a second loop defined by the third and fourth suture tails extending from the fourth entry point, to an exit point on the second surface of the graft and around opposite sides of the graft, the second loop surrounding the terminal length of the third and fourth suture tails such that the terminal length of the third and fourth suture tails is disposed between the first surface of the graft and the second loop. The method can also include repeatedly passing the second needle and the attached second suture through the first surface at second subsequent entry points longitudinally spaced apart from the third and fourth entry points in the second direction to the second surface to form second multiple loops, each of the second multiple loops spaced apart from adjacent second loops in the second direction and each loop surrounding the terminal length of the third and fourth suture tails such that the terminal length of the third and fourth suture tails is disposed between the second surface of the graft and the loop, and continuing the act of repeatedly passing until reaching a second final entry point in proximity to the second end of the graft.

In another aspect, a tissue repair construct is provided that includes a graft having first and second ends and a suture affixed to the graft. The suture extends along a portion of a length of the graft from an origin point remote from the first end of the graft, the suture has a pattern including multiple loops of suture spaced apart along the length of the graft and extending from the origin point to a terminal point adjacent to the first end of the graft, each loop overlaying a terminal length of each of two suture tails of the suture such that the terminal length of each suture tail is disposed between a first surface of the graft and the loop. Each loop is defined by adjacent portions of the suture tails passing through the first surface of the graft at one entry point to a second surface of the graft, each of the suture tails passing around opposite sides of the graft to another entry point spaced longitudinally from the origin point.

The tissue repair construct can vary in a number of ways. For example, in some embodiments, a number of the multiple loops ranges from three to eight.

The tissue repair construct can further include a second suture affixed to the graft and extending along a portion of a length of the graft from a second origin point remote from the second end of the graft, the second suture having a pattern comprising second multiple loops of suture spaced apart along the length of the graft and extending from the second origin point to a second terminal point adjacent to the second end of the graft, each loop overlaying a second terminal length of each of two second suture tails of the second suture such that the second terminal length of each suture tail is disposed between the first surface of the graft and the loop. Each of the second loops is defined by adjacent portions of the second suture tails passing through the first surface of the graft at one entry point to the second surface of the graft, each of the second suture tails passing around opposite sides of the graft to another entry point spaced longitudinally from the second origin point.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to systems and methods for preparing ligament grafts for ligament reconstruction, or augmentation, surgeries. A graft is prepared by reinforcing one or both end portions thereof to thus create a tissue repair construct. In some embodiments, a method is provided that includes preparing a tissue repair construct using a whip-stitching technique and reinforcing the graft and the stitching using free ends, or a terminal length, of suture tails of the suture being affixed to the graft. As a needle attached to the suture is passed through a first surface of the graft at a first entry point, the free ends of the suture tails remain positioned on the first surface of the graft so that multiple suture loops subsequently formed around and through the graft encompass the suture tails.

The systems and methods described herein may have a number of advantages over existing techniques for preparing ligament grafts. In particular, a graft is prepared using the described tissue repair construct in a simple and effective manner. Because the tissue repair construct is reinforced using the same suture that is used to form loops, reinforcing the construct does not increase the time required for the construct preparation. Furthermore, the reinforcement improves the overall strength of the tissue repair construct. Thus, the time required to prepare the graft can be reduced, which can reduce the overall time and cost of the surgery and mitigate risk to the patient. Also, the described graft preparation procedure is simplified and is less labor-intensive.

The described techniques can be used in conjunction with a variety of ligament grafts, including hamstring ligament grafts, and in a variety of different surgical contexts regardless of the type of ligament graft being used in a particular surgical procedure. The systems and methods described herein can be utilized in connection with preparing graft ligaments for repairing or replacing ligaments in a variety of joints, but can in some embodiments have particular utility in cruciate ligament reconstruction procedures. For example, the described techniques are used to prepare grafts used in ACL and/or PCL repair procedures.

Figure 1:
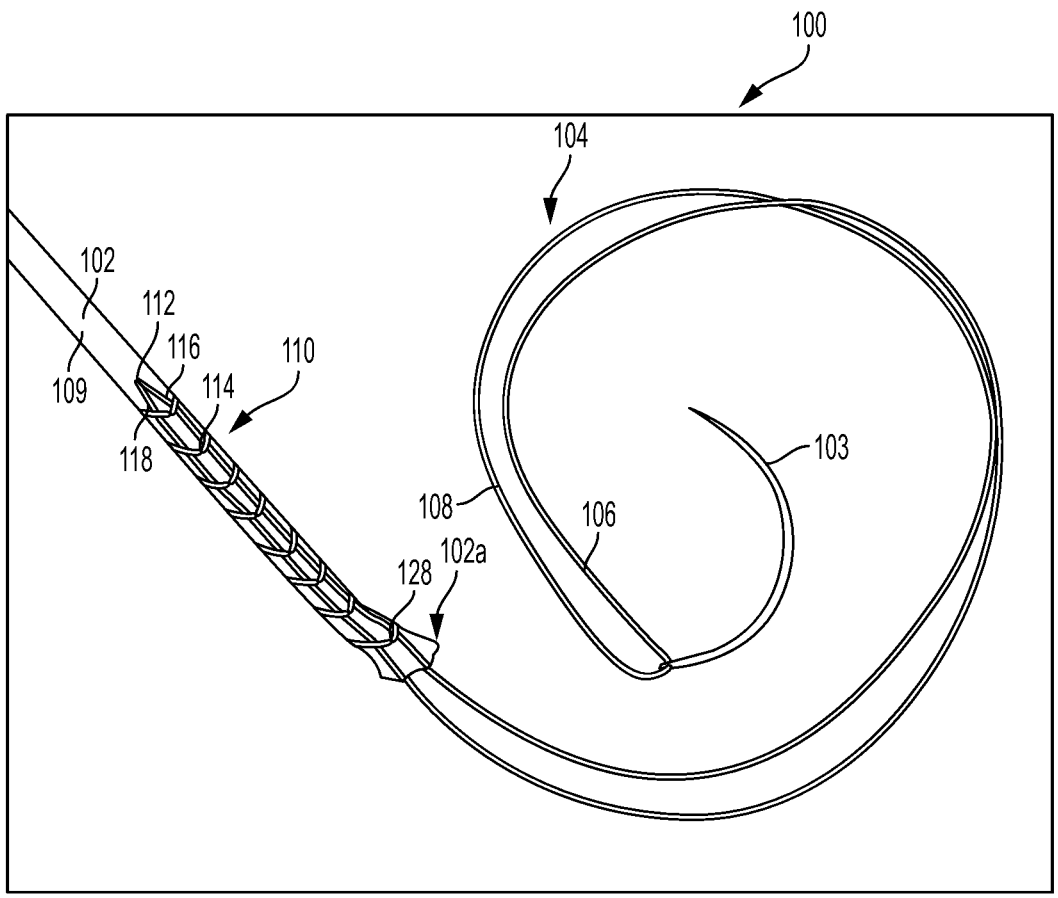
FIG. 1 is a schematic illustration of a graft prepared using reinforced whip-stitching in accordance with some embodiments.

FIG. 1 illustrates a tissue repair construct 100 in accordance with some embodiments that has an improved strength relative to a graft construct prepared using some existing techniques. As shown in FIG. 1, the tissue repair construct 100 includes a graft 102 having first and second ends (only a first end 102a is shown in FIG. 1) and a suture 104 having first and second suture tails 106, 108. The suture 104 is secured to the graft 102 by passing through the graft 102 and forming multiple loops 110 around the graft 102, as discussed in more detail below.

The graft 102 can be a tendon or any other type of graft, and it can include one or more graft bundles or strands. The first and second suture tails 106, 108 affixed to the graft 102 have respective free ends 116, 118 that are used to provide structural support for the tissue repair construct 110. As shown in FIG. 1, the suture 104 is passed through a first surface 109 of the graft 102 at a first entry point or origin point 112 that is remote from the first end 102a of the graft 102 so that a terminal length or free ends 116, 118 of each of the first and second suture tails 106, 108, respectively, remain positioned on the first surface 109 of the graft 202.

The suture 104 is passed through the first surface 109 of the graft 202 at the origin point 112 so that it exits from the second surface of the graft 102, opposite to the first surface 109, which is not shown in FIG. 1. As also shown in FIG. 1, the suture 104 affixed to the graft 102 has a pattern in the form of multiple suture loops 110 that are spaced apart along the length of the graft 102 and that extend from the origin point 112 to a terminal point 128 adjacent to the first end 102a of the graft 102. Each of the multiple suture loops 110 is defined by a portion of the first and second suture tails 106, 108 passing through the first surface 109 of the graft 102 at one entry point to the second surface of the graft 102 so that each of the suture tails 106, 108 passes around opposite sides of the graft to another entry point spaced longitudinally from the first or origin entry point 112.

In the illustrated embodiment, the suture loops 110 are formed in the direction towards the first end 102a of the graft 102. As shown in FIG. 1, to prepare the tissue repair construct 100, the first and second suture tails 106, 108 are attached to a needle, such as a needle 103. It should be appreciated that the needle 103 is shown in FIG. 1 for illustration purposes only, as the needle 103 is removed from the tissue repair construct 100 prior to using the construct 100 in a ligament replacement or augmentation procedure.

As shown in FIG. 1, the tissue repair construct 100 is reinforced using first and second free ends 116, 118 of the first and second suture tails 106, 108, respectively. Each of the suture loops 110, e.g., a first loop 110A formed by passing the first and second suture tails 106, 108 around the opposite sides of the graft 102 and through a second entry point 114 longitudinally spaced apart from the first entry point 112, has the first and second free ends 116, 118 disposed between the first surface 109 of the graft 102 and the loop 110A.

Figure 2:
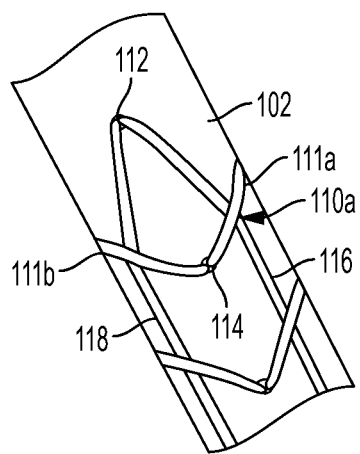
FIG. 2 is a schematic illustration of a portion of the graft of FIG. 1.

FIG. 2, illustrating a portion of the tissue repair construct 100, shows that the first loop 110A is formed so that its first and second portions 111a, 111b disposed around opposite sides of the graft 102 each have a respective one of the first and second free ends 116, 118 disposed underneath the first and second portions 111a, 111b. Thus, the first free end 116 of the first suture tail 106 is disposed between the first portion 111a of the loop 110A and the first surface 109 of the graft 102. The second free end 118 of the second suture tail 108 is similarly disposed between the second portion 111b of the loop 110A and the first surface 109 of the graft 102. In this way, the loop 110A locks down on the first and second free suture ends 116, 118 that are positioned on the surface 109 of the graft 102.

In the prepared tissue repair construct 100, the first and second free ends 116, 118 of the first and second suture tails 106, 108 are positioned on the first surface 109 of the graft 102 so that they are disposed along the sides of the graft 102, as shown in FIGS. 1 and 2. One skilled in the art will appreciate that the first and second free ends 116, 118 of the suture 104 can be positioned in other ways along the first surface of the graft. For example, the first and second free ends 116, 118 can be positioned on opposite surfaces of the graft 102. Furthermore, in one embodiment, the first and second free ends 116, 118 can be criss-crossed one or more times along the length of the graft 102.

Regardless of the way in which the first and second free ends 116, 118 are positioned on the surface of the graft 102, the first and second free ends 116, 118 function like a spine extending along the graft 102, thus improving the strength of the construct. In a typical graft preparation technique, at each pass through the surface of the graft 102, the needle 103 pierces the graft 102 approximately in the middle of the graft surface. Thus, the graft fibers can be moved apart by the needle piercing therethrough, which can lead to a certain degree of disintegration of graft fibers, which may ultimately cause weakening of the graft 102. The reinforcement features described herein, such as use of the first and second free ends 116, 118 on the surface of the graft so that they are encircled by the loops, strengthen the tissue repair construct 100 and improve load distribution when a load is applied to the graft 102. In particular, the first and second free ends 116, 118 help to distribute the load from the needle/suture entry points on the graft 102, so that a larger load can be applied without causing damage to tissue of the graft 102. Thus, the first and second free ends 116, 118 act as a "rip-stop" that helps to protect the graft tissue from being excessively deformed or ripped.

As discussed above, the needle 103 having the first and second suture tails 106, 108 of the suture 104 attached thereto is shown in FIG. 1 to illustrate that the free suture tails 106, 108 are passed through the graft 102 using the needle 103 with the suture tails 106, 108. After the multiple suture loops 110 are formed, the suture tails 106, 108 may be cut to be separated from the needle 103 so that a certain length of free ends of the suture tails 106, 108 remains attached to the first end 102a of the graft 102. These free ends, which are opposite to the first and second free ends 116, 118, are then used for insertion and fixation of the tissue repair construct 100 at an insertion site.

A length of the first and second free ends 116, 118 reinforcing the tissue repair construct 100 can vary in a number of ways. In the illustrated embodiment, the length of the first and second free ends 116, 118 can be equal or approximately equal to a length of a portion of the graft 102 that has the loops 110 formed thereon. Thus, the first and second free ends 116, 118 can extend from the origin point 112 to the terminal point 128 adjacent to the first end 102a of the graft 102. The first and second free ends 116, 118 can extend beyond the terminal point 128 towards the first end 102a of the graft 102 and they may extend only slightly (e.g., to a distance of less than 1 cm) or not extend at all beyond the first end 102a of the graft 102.

Alternatively, in some embodiments, one or both of the first and second free ends 116, 118 extend beyond the first end 102a of the graft 102 by a distance that is greater than 1 cm. For example, the first and second free ends 116, 118 can extend beyond the first end 102a of the graft 102 so that their length is approximately equal to a length of the free ends of the suture tails 106, 108 that are formed after the suture tails 106, 108 are separated from the needle 103. One skilled in the art will appreciate that the first and second free ends 116, 118 can have any suitable length, as the described embodiments are not limited in this respect.

The suture 104, as well as other sutures that are used in the described graft preparation techniques, can be formed from any suitable materials. In some embodiments, the suture can be from size 0 to size 5, such as Orthocord™ suture commercially available from DePuy Mitek, and Ethibond™ suture available from Ethicon, Inc. Orthocord™ suture is approximately fifty-five to sixty-five percent PDS™ polydioxanone, which is bioabsorbable, and the remaining percent includes ultra high molecular weight polyethylene, while Ethibond™ suture is primarily high strength polyester. In some embodiments, the issue repair construct can be formed from ultra-high-molecular-weight polyethylene (UHMWPE). In some embodiments, the construct can include High-Molecular Weight-polyethylene (HMWPE) sutures or HMWPE sutures with a co-braid (e.g., monofilament polypropylene, nylon or other co-braid). In some embodiments, monofilament sutures such as, for example, Monocryl® available from Ethicon, Inc., may be utilized. As another example, an absorbable suture such as Vycryl® (a copolymer made from 90% glycolide and 10% L-lactide) also available from Ethicon, Inc. may be used. The sutures used herein can have any suitable amount and type of bioabsorbable material, which can depend on a particular surgical procedure and/or surgeon preferences.

Figure 4:
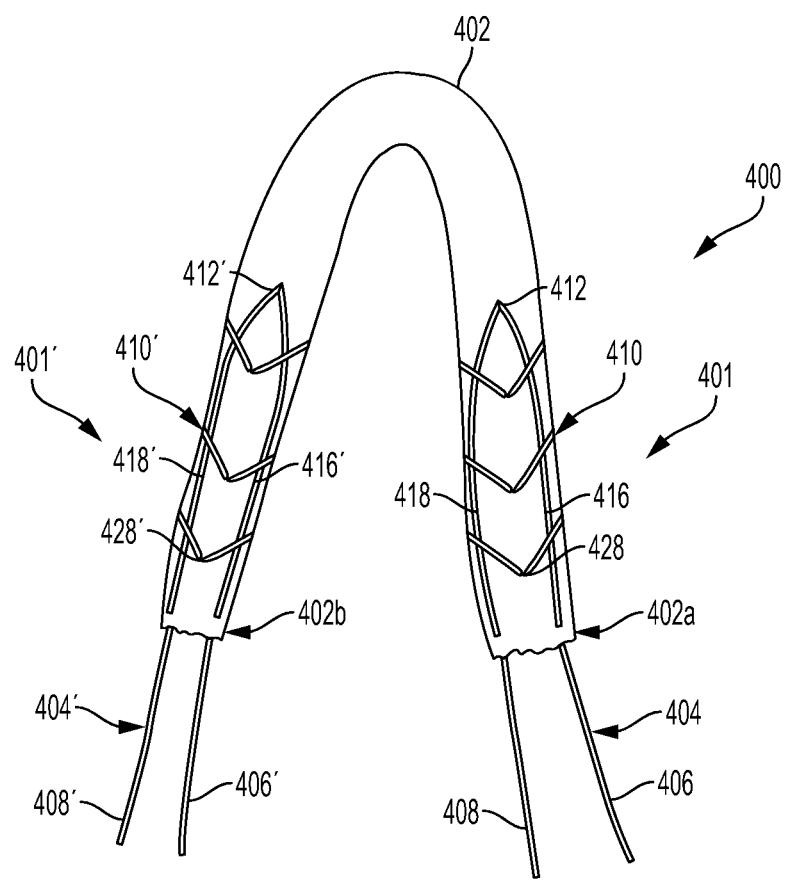
FIG. 4 is a schematic illustration of one embodiment of a graft having both ends thereof prepared using the described techniques.

It should be appreciated that although the tissue repair construct 100 is shown on one end of the graft 102 in FIG. 1, a similar tissue repair construct can be formed on both ends of the graft, as shown in FIG. 4. Furthermore, multiple grafts can be used during a surgery, with one or both ends of each of the grafts being prepared as shown in FIG. 1.

Figure 3A:
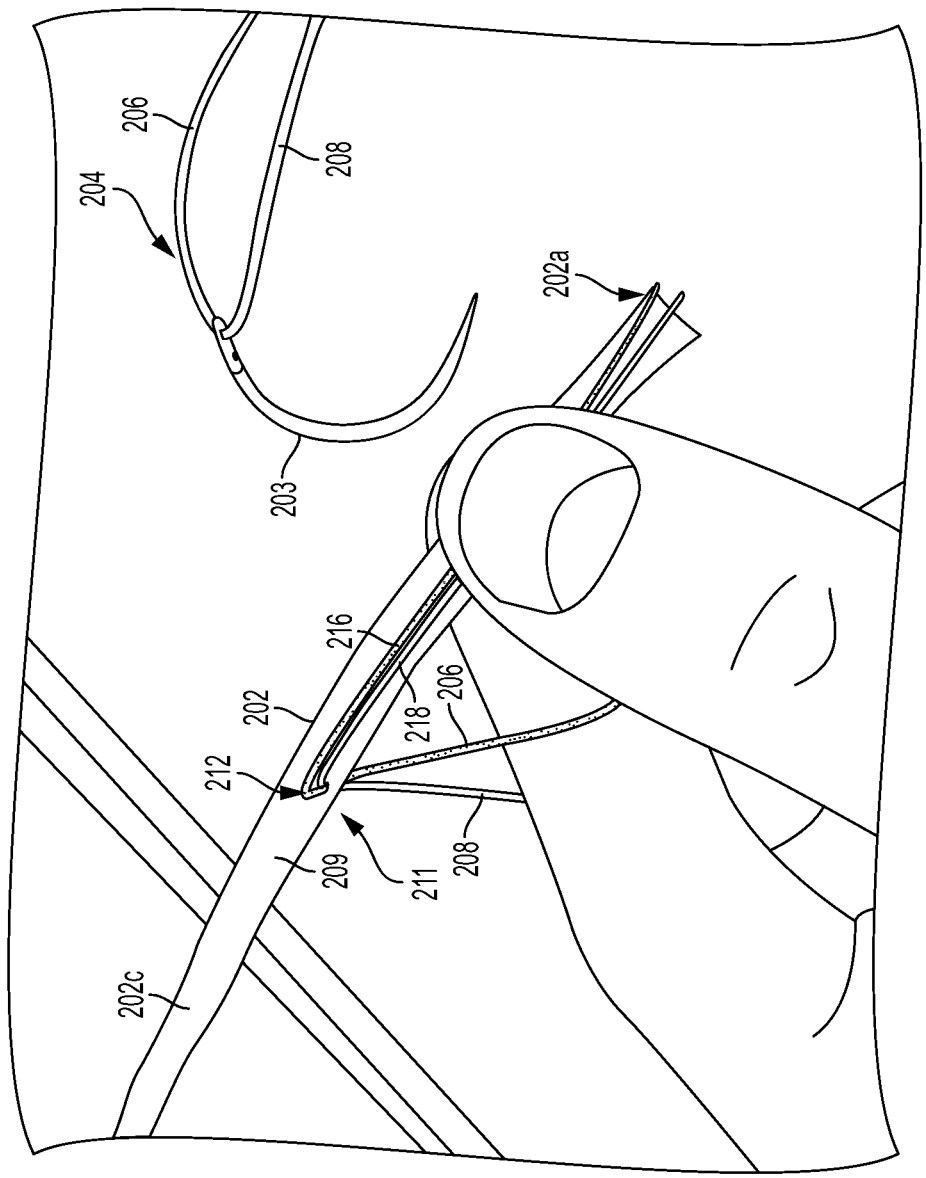
FIGS. 3A-3D are schematic illustrations of one embodiment of a method of preparing a tissue repair construct.

FIGS. 3A-3D illustrate one embodiment of a method of preparing a tissue repair construct 200, which can be similar to tissue repair construct 100 shown in FIGS. 1 and 2. As shown in FIG. 3A, a needle 203 has first and second suture tails 206, 208 of a suture 204 attached thereto (a portion of the first and second suture tails 206, 208 is shown). The needle 203 can be attached to the first and second suture tails 206, 208 in any suitable manner. For example, the suture 204 can be passed through an eyelet formed in the needle 203. In some embodiments, the needle 203 can be coupled to the suture 204 via an intermediate feature, such as a small suture loop or other feature connected to the needle 203 and to the suture 204. Such intermediate feature can facilitate the stitching.

In the illustrated embodiment, the suture 204 is attached to the needle 203 so that the needle 203 is positioned approximately in the middle of the suture 204 and the first and second suture tails 206, 208 have approximately the same length. However, it should be appreciated that the first and second suture tails 206, 208 can have any suitable lengths, including different lengths.

As shown in FIG. 3A, the needle 203 having the first and second suture tails 206, 208 attached thereto is passed through a first surface 209 of the graft 202 at a first entry or origin point 212 so that the needle 203 and a portion of the suture tails 206, 208 are passed to a second, opposite surface 211 of the graft 202. In the illustrated embodiment, the first entry point 212 is remote from a first end 202a of the graft 202. The first entry point 212 can be located a suitable distance apart from the first end 202a. In some embodiments, that distance is approximately a half of a length of the graft 202. However, in other embodiments, the distance is less than the half-length of the graft 202. For example, in some embodiments, a distance between the first entry point 212 and the first end 202a of the graft 202 is from about 0.5 cm to about 6 cm. In some embodiments, the distance between the first entry point 212 and the first end 202a of the graft 202 is from about 2 cm to about 4 cm.

As also shown in FIG. 3A, the needle 203 with the first and second suture tails 206, 208 attached thereto is passed through the first surface 209 of the graft 202 at the origin point 212 so that a terminal length of each of the first and second suture tails 206, 208 is maintained on the first surface 209 of the graft 202. The terminal length or free suture ends 216, 218 of the first and second suture tails 206, 208 extend in a first direction from the first entry point 212 towards the first end 202a of the graft 202. In the illustrated embodiment, the first direction is from an intermediate portion 202c of the graft towards the first end 202a thereof. The free suture ends 216, 218 can be held on the first surface 209 of the graft 202 while being tensioned. The free suture ends 216, 218 thus serve as a structural support that reinforces the graft 202.

As shown in FIG. 3A, the free suture ends 216, 218 extending from the first entry point 212 have a length approximately equal to the length of a portion of the graft 202 from the first entry point 212 to the first end 202a of the graft 202. However, as mentioned above, free suture ends, such as free suture ends 216, 218, can have any suitable length. The free suture ends 216, 218 can be trimmed to an appropriate length, if desired.

Figure 3B:
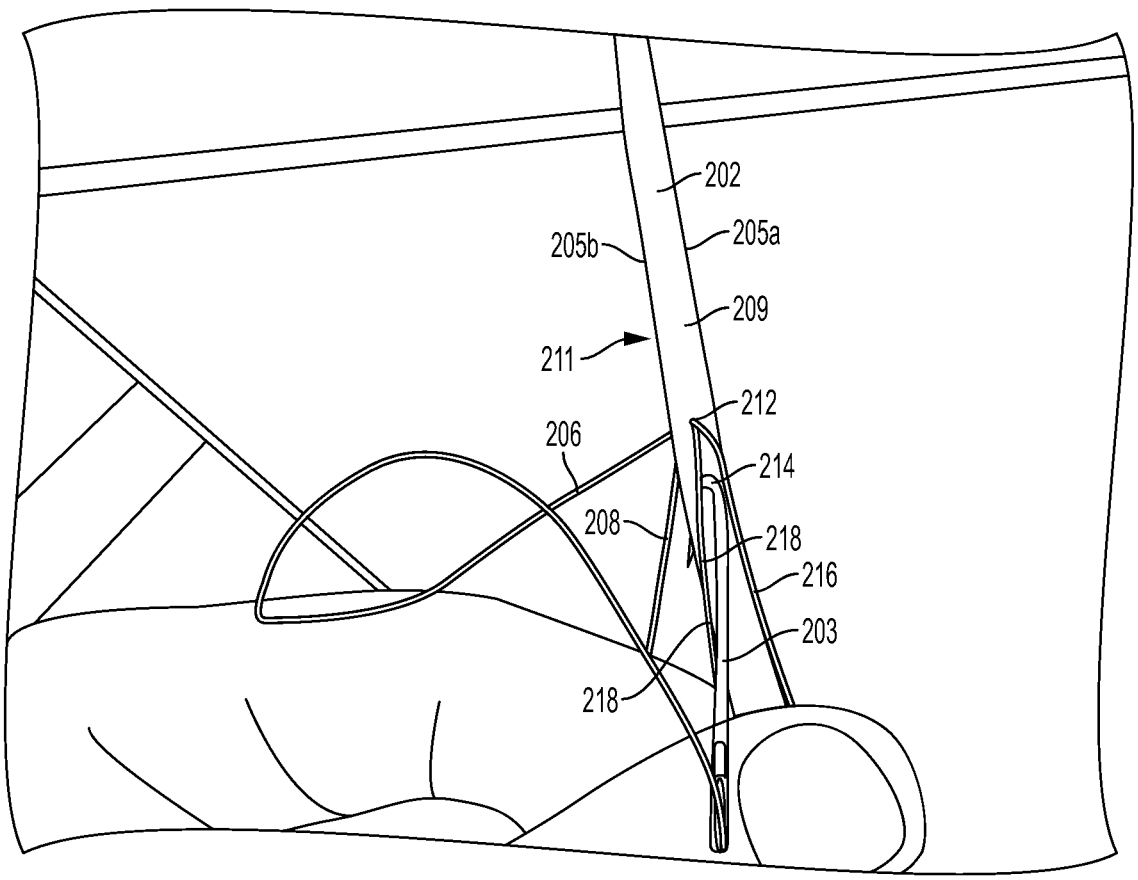

As shown in FIG. 3B, to form a first loop 210A (FIG. 3C), the needle 203 having the first and second suture tails 206, 208 attached thereto and extending from the second side 211 of the graft 209 is passed around the first end 202a of the graft 202 so that the first and second suture tails 206, 208 are passed around opposite side surfaces 205a, 205b of the graft 202. The needle 203 then pierces the first surface 209 of the graft 202 at a second entry point 214 longitudinally spaced apart from the first entry point 212 in the first direction. As also shown in FIG. 3B, the needle 203 is advanced through the graft 202 while being positioned between the free suture ends 216, 218 extending on both sides of the second entry point 214.

Figure 3C:
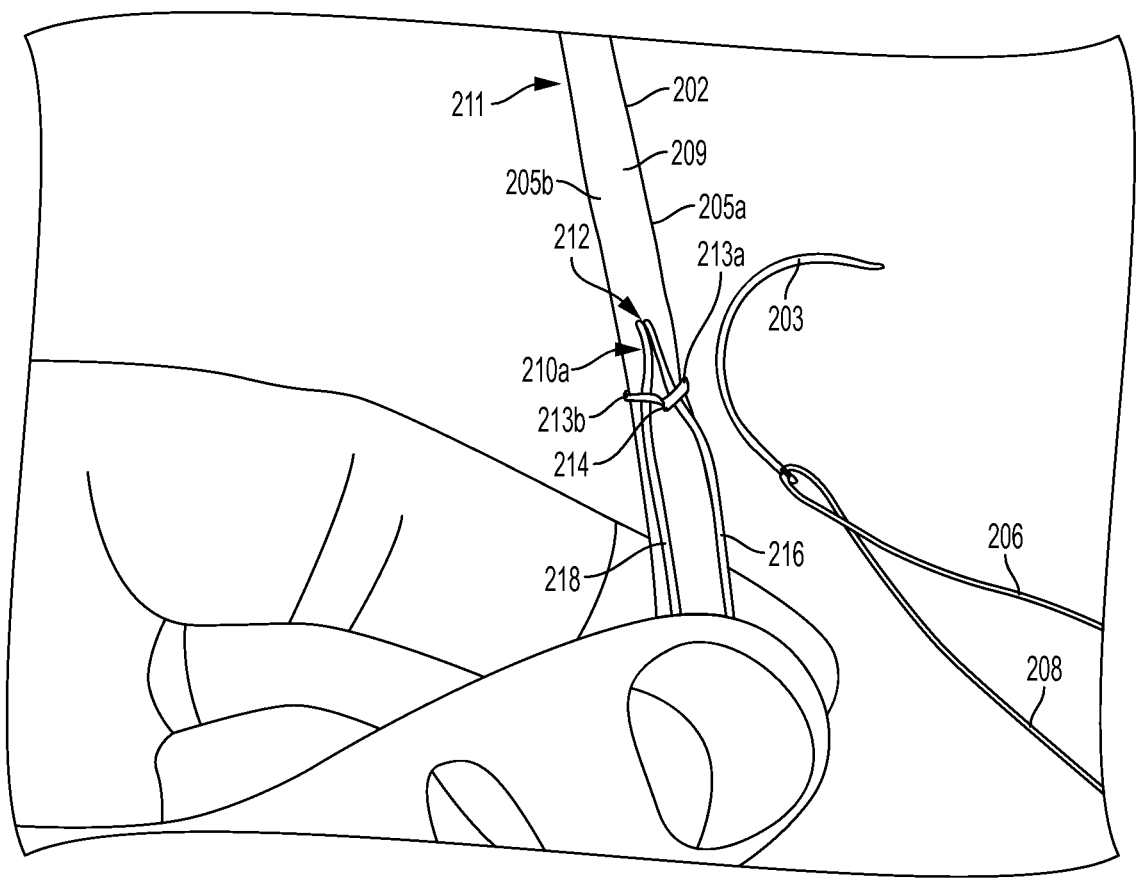

The needle 203 with the attached first and second suture tails 206, 208 is passed through the graft 202 from its first surface 209 to the second surface 211, and then extended so that the first and second suture tails 206, 208 are passed through the graft 202 to thereby form the first loop 210A as shown in FIG. 3C. The first loop 210A is formed so that the first and second suture tails 206, 208 are disposed around opposite side surfaces 205a, 205b of the graft 202 and so that the loop 210A is defined by the suture tails 206, 208 extending from the second entry point 214, to an exit point (not shown in FIG. 3C) on the second surface 211 of the graft 202 and around the opposite sides 205a, 205b of the graft 202.

Figure 5:
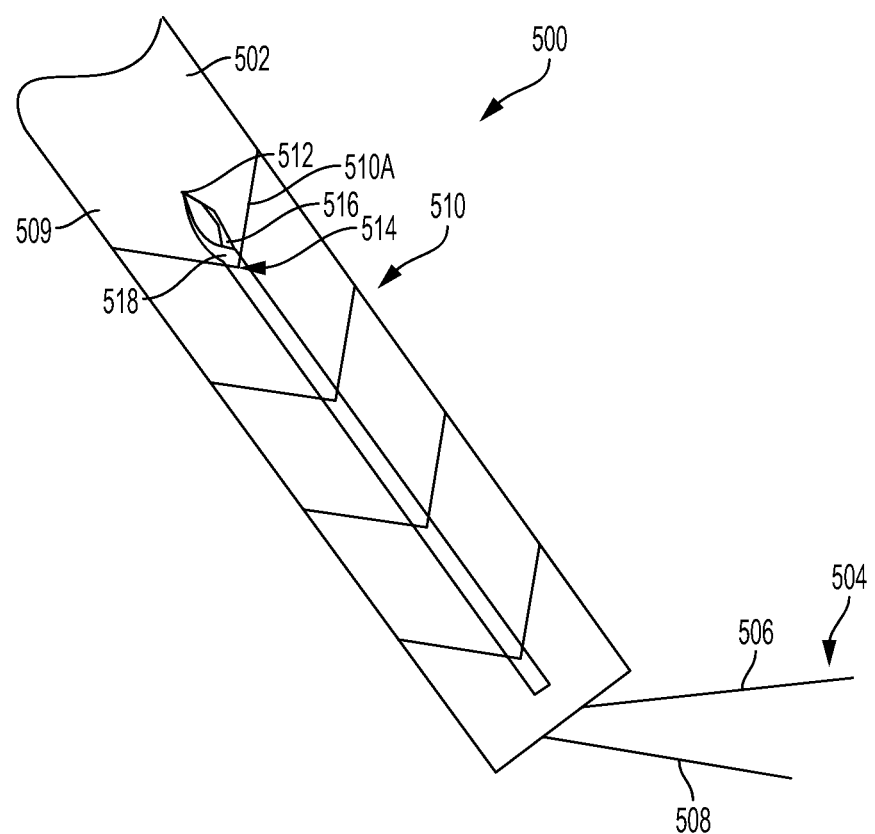
FIG. 5 is a schematic illustration of a graft prepared using reinforced whip-stitching in accordance with some embodiments.

In some embodiments, as shown in more detail below with regard to FIG. 5, the needle penetrates through one or both of the terminal free suture ends 216, 218. In this way, one or both of the free suture ends 216, 218 can be locked down and at least some of the fibers of the free suture end(s) serve to bolster the strength of the stitching.

As shown in FIG. 3C, first and second portions 213a, 213b of the loop 210A formed by the first and second suture tails 206, 208, respectively, overlay the terminal lengths or free suture ends 216, 218 of the first and second suture tails 206, 208 such that the terminal lengths 216, 218 are disposed between the first surface 209 of the graft 202 and the loop 210A. For example, the first free suture end 216 is disposed between the first surface 209 of the graft 202 and the first portion 213a of the loop 210A. Similarly, the second free suture end 218 is disposed between the first surface 209 of the graft 202 and the second portion 213b of the loop 210A. Thus, the loop 210A holds the free suture ends 216, 218 in place so that the free suture ends 216, 218 extend along the opposite side surfaces 205a, 205b of the graft 202.

The needle 203 with the attached first and second suture tails 206, 208 is then repeatedly passed through the first surface 209 of the graft 202 at subsequent entry points longitudinally spaced apart from the first and second entry points 212, 214 in the first direction to the second surface 211 to form multiple loops. In this way, a tissue repair construct 200 shown in FIG. 3D is created.

Figure 3D:
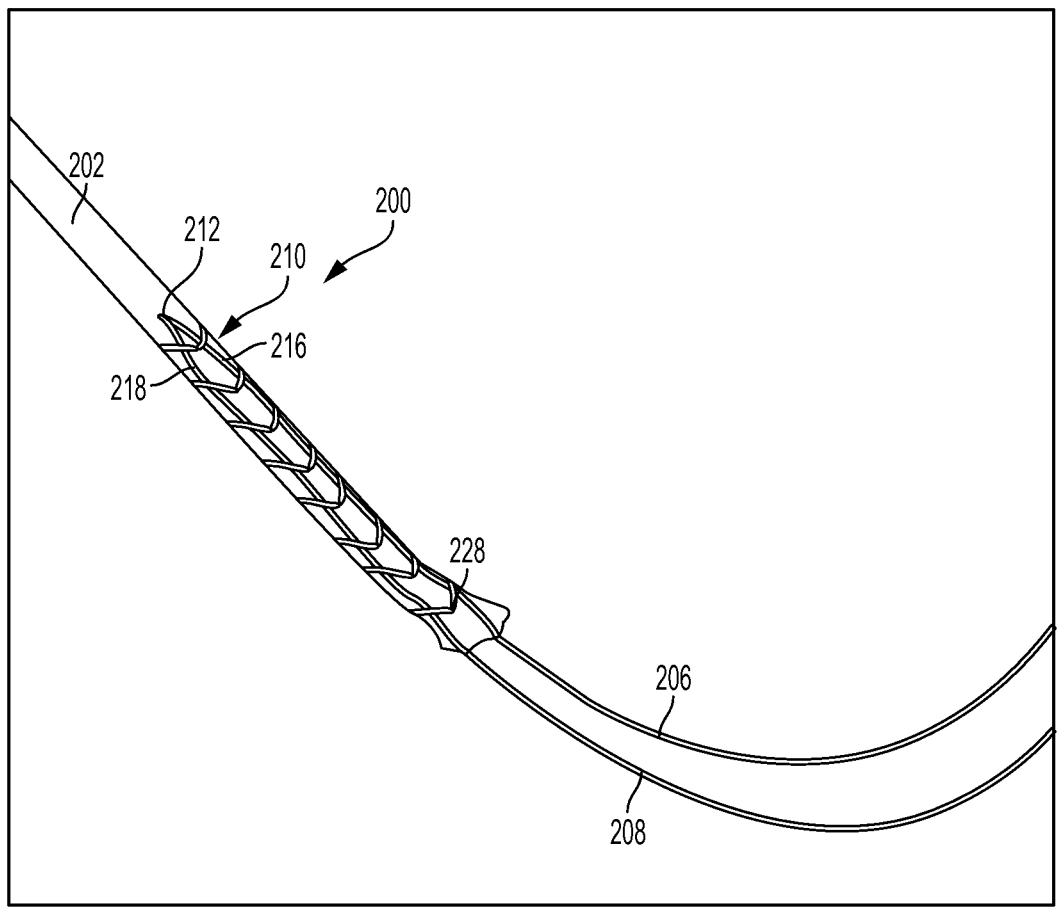

As shown in FIG. 3D, each of the multiple loops is spaced apart from adjacent loops in the first direction and each loop is formed such that the terminal length of the suture tails is disposed between the first surface of the graft and the loop. The needle 203 with the first and second suture tails 206, 208 is repeatedly passed through the first surface 209 of the graft 202 in the manner explained above until a final entry point 228 in proximity to the first end 202a of the graft 202 is reached. One skilled in the art will appreciate that the final entry point can be positioned at any suitable distance from the first end 202a of the graft 202.

After the multiple loops are formed, the suture 204 can be cut off to separate the suture tails 206, 208 from the needle 203. As a result, as shown in FIG. 3D, a suitable length of free ends of the suture tails 206, 208 can extend from the first end 202a of the graft 202. The free ends of the suture tails 206, 208 are used to advance the tissue repair construct in a tunnel prepared for a ligament repair procedure, or in another surgical site receiving the graft 202.

In some embodiments, the tissue repair construct 200 is formed so that a length of the free suture ends 216, 218 having at least a portion thereof disposed along a portion of a length of the graft 202 is approximately equal to a length of the free ends of the suture tails 206, 208 shown in FIG. 3D. In this way, an increased number of free suture ends is used for graft insertion and fixation, which can improve the strength of the attachment of the graft to the surgical site while allowing an increased tension to be applied to the graft. For example, the multiple free suture ends can be useful for certain fixation techniques (e.g., wrapping around a tibial post) where a larger number of sutures can provide more secure graft fixation.

Although not shown in FIGS. 3A-3D, in some embodiments, in addition to suture loops 210, additional stitches can be applied to the graft 202 in any suitable pattern, to additionally increase the strength of the fixation of the suture 204 to the graft. The additional stitches can be formed from the suture 204 in proximity to the first end 202a of the graft 202 to additionally increase the strength of the fixation of the suture 204 to the graft. Furthermore, as discussed below tissue repair construct such as the tissue repair construct 200 can be formed on another, second end of the graft 202 opposite to the first end 202a of the graft 202 so that both end portions of the graft 202 are prepared using the described techniques.

A person skilled in the art will appreciate that the suture loops, such as suture loops 110 (FIGS. 1 and 2) or suture loops 210 (FIGS. 3A-3D), can be formed in other ways different from the manner as shown in FIGS. 3A-3D. Regardless of the way in which the suture loops are formed to prepare a tissue repair construct, the tissue repair construct includes a terminal length of each of the suture tails disposed on a surface of the graft between the surface and the loops so as to provide a "spine" reinforcing the graft.

A tissue repair construct in accordance with some embodiments can be formed such that the suture reinforcement structure is present on both of the opposite end portions of the graft. For example, in one exemplary embodiment illustrated in FIG. 4, a tissue repair construct 400 has suture reinforcement portions or regions 401, 401' formed on portions of a graft 402 proximate to first and second ends 402a, 402b of the graft 402, respectively. The graft 402 can be any suitable type of graft, which can be harvested and prepared for suture attachment in any suitable manner, as known in the art.

The suture reinforcement regions 401, 401' of construct 400 can have any suitable configurations. As shown in FIG. 4, the graft 402 can have multiple loops 410 formed of first and second suture tails 406, 408 of a suture 404 attached thereto. The suture loops 410 are spaced along a length of the graft 402 from an origin entry point 412 to a terminal entry point 428 proximate to the first end 402a. As shown, each of the suture loops 410 is formed so that free suture ends 416, 418 of the first and second suture tails 406, 408 are disposed on a surface of the graft 402, between the surface and the loop. In a similar manner, multiple suture loops 410' formed of first and second suture tails 406', 408' of a suture 404' are spaced along a length of the graft 402 from an origin entry point 412' to a terminal entry point 428' proximate to the second end 402b of the graft 402. Each of the suture loops 410' is formed so that free suture ends 416', 418' of the first and second suture tails 406', 408' are disposed on a surface of the graft 402, between the surface and the loop.

One skilled in the art will appreciate that three loops of each of the multiple suture loops 410, 410' are shown by way of example only, as the suture reinforcement regions 401, 401' can include any suitable number of loops, including a different number of loops among the regions 401, 401'. For example, in some embodiments, a number of the loops formed in each of the suture reinforcement regions 401, 401' can range from three to eight. However, other number of loops can be formed. A desired number of loops can depend on characteristics of the graft (e.g., its size, condition, number of bundles used, etc.), a type of the surgery, a nature of the damage at the surgical site, and any other factors.

The suture reinforcement regions 401, 401' can be formed in any suitable order. For example, the suture reinforcement region 401 can be formed first and then the suture reinforcement region 401' can be prepared, or vice versa. One or both ends of the graft 402 can be held steady using suitable graft preparation equipment. For example, the DePuy Mitek Graft Preparation System can be utilized.

One skilled in the art will appreciate that the suture reinforcement regions 401, 401' can vary in any number of ways. For example, different suture reinforcement regions can be formed on opposite ends of the graft. Furthermore, the free suture ends 416, 418, 416', 418' are shown in FIG. 4 to terminate in proximity to the first and second ends 402a, 402b of the graft 402, respectively, by way of example only. The first and second suture tails 406, 408, 406', 408' and free suture ends 416, 418, 416', 418' can have any suitable lengths. Furthermore, the suture reinforcement regions 401, 401' can be formed so that the free suture ends reinforcing the tissue repair construct are formed on the same or opposite surfaces of the graft.

It should be appreciated that although illustrated embodiments provide techniques for preparing anterior or posterior cruciate ligaments for ligament reconstruction surgery, the techniques can be adapted for preparation of grafts for repair of other ligaments as well. For example, the described method can be used to prepare grafts for proximal or distal biceps repair.

Having thus described some examples of the described embodiments, various alterations, modifications, and improvements will readily occur to those skilled in the art. For example, in some embodiments, as suture loops of a tissue repair construct are formed, free suture ends of the suture can be penetrated through by a needle having tails of the suture attached thereto. Thus, FIG. 5 shows one embodiment of a tissue repair construct 500 that is formed so that terminal lengths or first and second free suture ends 516, 518 of first and second suture tails 506, 508 of a suture 504 positioned on a surface of a graft are locked to the graft 502 by being penetrated therethrough.

A needle (not shown) can be attached to the first and second suture tails 506, 508 of the suture 504 in any suitable manner. FIG. 5 illustrates that the needle with the first and second suture tails 506, 508 attached thereto is passed through a first surface 509 of the graft 502 at a first entry point 512 to exit from an opposite, second surface of the graft. The free suture ends 516, 518 of the first and second suture tails 506, 508 remain on the first surface 509 of the graft 502, as shown in FIG. 5. In the illustrated embodiment, at least a portion of one or both of the free suture ends 516, 518 can be wider than the rest of the suture 504 so that, as shown in FIG. 5, one of the free suture ends 516, 518 can be at least partially disposed over the other of the free suture ends 516, 518.

After the first and second suture tails 506, 508 are then passed around opposite side surfaces of the graft 502, the needle with the suture tails 506, 508 can pass through the first surface 509 at a second entry point 514. In the illustrated embodiment, as the needle with the suture tails 506, 508 passes through the first surface 509 at the second entry point 514, it also penetrates through one or both of the free suture ends 516, 518. As shown in FIG. 5, the second free suture end 518 can be positioned over the first free suture end 516 and the needle can thus pass through both of the first and second free suture ends 516, 518 and then pass through the first surface 509 of the graft 502 at the second entry point 514 to create a first loop 510A. In this way, the suture loop 510A overlays the free suture ends 516, 518 such that the free suture ends 516, 518 are disposed between the first surface 509 of the graft 502 and the loop. The process can then continue in a similar manner to form multiple suture loops 510 of the tissue repair construct 500, as shown in FIG. 5.

One skilled in the art will appreciate that the needle can pass through both or one of the free suture ends 516, 518. Thus, even though in FIG. 5 the first free suture end 516 is positioned at least partially underneath the second free suture end 518 along almost the entirety of a length of the free suture ends 516, 518, the free suture ends 516, 518 can only partially overlap (e.g., which different degrees of overlap throughout their length), or they may not overlap at all. The free suture ends 516, 518 can be positioned in any manner with respect to each other. In this way, the needle with the first and second suture tails 506, 508 attached thereto can pass through either or both of the free suture ends 516, 518. Furthermore, the needle can pass through one or both of the free suture ends 516, 518 at each of the entry points or at only some of the entry points.

The free suture ends 516, 518 can have any suitable width. For example, in one embodiment, the width of one or both of the free suture ends 516, 518 can range from about 2 mm to about 4 mm. However, one skilled in the art will appreciate that the free suture ends 516, 518 can have other widths.

The free suture ends 516, 518 can have any suitable configuration. In some embodiments, one or both of the free suture ends 516, 518 can be at least partially flat so that they are easier to penetrate therethrough than a suture with a round or approximately round cross-section. For example, one or both of the free suture ends 516, 518 can be tape-like or ribbon-like or they can be in any other form. The free suture ends 516, 518 can be flattened throughout their entire lengths or at portions thereof. The free suture ends 516, 518 can be formed as at least partially flat in a number of ways. For example, the suture 504 can be flattened (e.g., mechanically and/or by heat, etc.). Additionally or alternatively, the wider portion can be created by braiding, weaving, crocheting, knitting, or otherwise manipulating the suture 504. Furthermore, in some embodiments, the portion of the suture forming the free suture ends 516, 518 can be one or more separate elements that can be attached to the suture tails 506, 508 in a suitable manner.

The above alterations, modifications, and improvements are intended to be within the spirit and scope of the described embodiments. Accordingly, the foregoing description is by way of example only, and not intended to be limiting.

What is claimed is:

1. A tissue repair construct, comprising:
a graft having first and second ends; and
a first suture affixed to the graft and extending along a first portion of a length of the graft, the first suture comprising first and second suture portions and first and second suture tails, wherein the first and second suture portions are configured to form a pattern comprising a first plurality of loops,
the first plurality of loops configured to be spaced apart along the first portion of the length of the graft, the first plurality of loops configured to overlay a terminal length of the first and second suture tails such that at least a portion of the terminal length of the first and second suture tails are disposed between a first surface of the graft and the first plurality of loops.

2. The tissue repair construct of claim 1, wherein the first plurality of loops range from three to eight loops.

3. The tissue repair construct of claim 2, wherein at least one of the first and second suture tails extends a distance beyond the first end of the graft.

4. The tissue repair construct of claim 1, further comprising:
   a second suture affixed to the graft and extending along a second portion of the length of the graft, the second suture configured to form a pattern comprising a second plurality of loops,
   wherein the second suture includes third and fourth suture tails,
   the second plurality of loops configured to be spaced apart along the second portion of the length of the graft, one or more of the second plurality of loops configured to overlay a terminal length of one or more of the third and fourth suture tails such that at least a portion of the terminal length of one or more of the third and fourth suture tails is disposed between the first surface of the graft and the loop.

5. The tissue repair construct of claim 4, wherein the second plurality of loops range from three to eight loops.

6. The tissue repair construct of claim 5, wherein at least one of the third and fourth suture tails extends a distance beyond the second end of the graft.

7. The tissue repair construct of claim 4, wherein at least one of the third and fourth suture tails extends a distance beyond the second end of the graft.

8. The tissue repair construct of claim 1, wherein at least one of the first and second suture tails extends a distance beyond the first end of the graft.

9. A method of graft preparation, comprising:
   passing a suture having first and second suture portions having first and second suture tails through a first surface of a graft at a first location, remote from a first end of the graft, to a second surface of the graft, opposite the first surface, while maintaining a terminal length of each of the first and second suture tails on the first surface of the graft such that the terminal length of the first and second suture tails extend in a first direction from the first location toward the first end of the graft;
   passing the first and second suture portions from the second surface of the graft, around opposite exterior sides of the graft to the first side of the graft, and through the first surface of the graft at a second location, longitudinally spaced apart from the first location, back to the second surface of the graft so that the first and second suture portions form a loop around the graft defined by the first and second suture portions, wherein the loop surrounds the terminal length of the first and second suture tails such that the terminal length of the first and second suture tails is disposed between the first surface of the graft and the loop;
   repeatedly passing the suture from the first surface at primary subsequent locations longitudinally spaced apart from the first and second locations in the first direction to the second surface to form multiple loops, each of the multiple loops spaced apart from adjacent loops in the first direction and each loop surrounding the terminal length of the first and second suture tails such that the terminal length of the suture tails is disposed between the first surface of the graft and the loop; and
   continuing the act of repeatedly passing until reaching a final location in proximity to the first end of the graft.

10. The method of claim 9, wherein the terminal length of the of each of the first and second suture tails is approximately equal to a length of a portion of the graft between the first location and the first end of the graft.

11. The method of claim 9, wherein the suture tails extend beyond the first end of the graft.

12. The method of claim 9, wherein the suture comprises a continuous suture.

13. The method of claim 9, wherein the multiple loops range from three to eight loops.

14. The method of claim 9, wherein passing the suture from the first surface at the second and subsequent locations comprises passing the suture between first and second suture tails.

15. The method of claim 9, further comprising:
    passing a second suture having third and fourth suture portions having third and fourth suture tails through the first surface of the graft at a third location, remote from the second end of the graft, to the second surface of the graft while maintaining a terminal length of each of the third and fourth suture tails on the first surface of the graft such that the terminal length of the third and fourth suture tails extend in a second direction from the third location towards the second end of the graft;
    passing the third and fourth suture portions from the second surface of the graft, around opposite exterior sides of the graft to the first side of the graft, and through the first surface of the graft at a fourth location, longitudinally spaced apart from the third location, back to the second surface of the graft so that the third and fourth suture portions form a second loop around the graft defined by the third and fourth suture portions, wherein the second loop surrounds the terminal length of the third and fourth suture tails such that the terminal length of the third and fourth suture tails is disposed between the first surface of the graft and the second loop;
    repeatedly passing the second suture from the first surface at secondary subsequent locations spaced apart from the third and fourth locations in the second direction to the second surface to form second multiple loops, each of the second multiple loops spaced apart from the adjacent second loops in the second direction and each loop surrounding the terminal length of the third and fourth suture tails such that the terminal length of the third and fourth suture tails is disposed between the second surface of the graft and the loop; and
    continuing the act of repeatedly passing until reaching a second final location in proximity to the second end of the graft.

16. The method of claim 15, wherein the terminal length of each of the third and fourth suture tails is approximately equal to a length of a portion of the graft between the third location and the second end of the graft.

17. The method of claim 15, wherein the third and fourth suture tails extend beyond the second end of the graft.

18. The method of claim 15, wherein the second suture comprises a continuous suture.

19. The method of claim 15, wherein the second multiple loops range from three to eight loops.

20. The method of claim 15, wherein passing the second suture from the first surface at the fourth and subsequent locations comprises passing the suture between third and fourth suture tails.

* * * * *